United States Patent [19]

Benneche et al.

[11] Patent Number: 4,539,324
[45] Date of Patent: Sep. 3, 1985

[54] SUBSTITUTED PYRIMIDIN-2-ONES AND THE SALTS THEREOF

[75] Inventors: Tore Benneche; Per Strande; Kjell Undheim, all of Oslo, Norway

[73] Assignee: Nyegaard & Co. A/S, Oslo, Norway

[21] Appl. No.: 469,232

[22] Filed: Feb. 24, 1983

[30] Foreign Application Priority Data

Feb. 24, 1982 [GB] United Kingdom ............... 8205483

[51] Int. Cl.³ .................. A61K 31/505; C07D 409/12; C07D 405/12; C07D 239/36
[52] U.S. Cl. ................................. 514/274; 544/296; 544/316; 544/318
[58] Field of Search .................. 544/316, 318, 296; 424/251

[56] References Cited

U.S. PATENT DOCUMENTS 4,399,140 8/1983 Gacek ................................. 424/251

OTHER PUBLICATIONS

Burger, Medicinal Chemistry, 3rd Ed., pp. 74–76, (1970).

Primary Examiner—Robert Gerstl
Attorney, Agent, or Firm—Bacon & Thomas

[57] ABSTRACT

Compounds of the general formula:

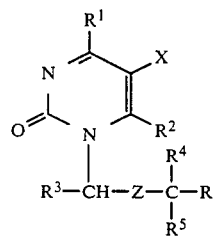

wherein
X represents halogen or trifluoromethyl;
$R^1$ and $R^2$, independently represent hydrogen or lower alkyl;
$R^3$, $R^4$ and $R^5$, which may be the same or different, each represent hydrogen, lower alkyl, lower alkenyl, lower alkynyl, lower alkanoyl, lower alkenoyl, $C_{7-16}$ aralkyl or $C_{6-10}$ aryl or a 5–9 membered unsaturated or aromatic heterocyclic ring; one or both of $R^4$ and $R^5$ may also represent aroyl groups;
Z represents an oxygen atom or a sulfur atom or oxide thereof or a group $NR^6$ (wherein $R^6$ is as defined for R hereinafter or represents the group $COR^7$ in which $R^7$ represents hydrogen or optionally substituted aryl, heterocyclic, aralkyl, lower alkyl or lower alkoxy group; and
R represents a $C_{6-10}$ carbocyclic aromatic group or a heterocyclic group containing a 5–9 membered unsaturated or aromatic heterocyclic ring which ring contains one or more heteroatoms selected from O, N and S and optionally carries a fused ring which carbocyclic or heterocyclic group may carry one or more $C_{1-4}$ alkyl or phenyl groups said groups being optionally substituted; and where acid or basic groups are present, the salts thereof are useful in combating abnormal cell proliferation.

The compounds of the invention are prepared by inter alia alkylation, ring closure and oxidation.

12 Claims, No Drawings

SUBSTITUTED PYRIMIDIN-2-ONES AND THE SALTS THEREOF

The present invention relates to substituted pyrimidin-2-ones, the salts thereof, processes for their preparation and pharmaceutical compositions containing them.

Abnormal cell proliferation is present in a number of diseases such as cancers, leukaemias, cutaneous cellular proliferation, e.g. contact dermatitis or psoriasis, or auto-immune diseases where proliferation of lymphocytes leads to an undesirable immune response against some of the normal tissues of the body.

A number of drugs are known which combat abnormal cell proliferation by destroying the cells in one of the phases of cell-division in which they are particularly susceptible to such attack. In general, the cell-division cycle of both normal and abnormal cells includes a succession of phases, usually termed the G1, S, G2 and M phases, the last-mentioned being mitosis which in itself includes four well defined phases, prophase, metaphase, anaphase and telophase, related to the rearrangement of chromasomal material in the cell. In general, DNA synthesis takes place in the S phase, while protein synthesis takes place in the G1 and G2 phases. The S phase is usually significantly longer than the G1, G2 and mitotic phases.

However, the cells are not normally dividing synchronously and at the time of administration of a particular drug a random proportion of both normal and abnormal cells will be in a phase susceptible to attack. This means that the drug may be indiscriminate in its effects and if the treatment is at a dose level significantly effective against abnormal cells, a large number of body cells may also be irreversibly damaged.

The present invention is based, in part, on the concept of using a drug to arrest the cell-division cycle reversibly in a particular phase, namely the metaphase, so that during the period when an effective amount of the drug remains in the system, a large number of both normal and abnormal cells reach that phase and stop dividing. When the drug has been eliminated from the system, cell division is resumed by affected cells and is initially synchronous. However, the normal and abnormal cells usually divide at markedly different rates and, considering the cells affected by the drug, after a few hours the abnormal cells will be synchronously in one phase while the normal cells will be in another. It is then possible to administer a drug which is effective against cells in the phase reached by the abnormal cells but not effective against cells in the phase reached by the normal cells. Thus, for example, hydroxyurea and cytosine arabinoside are effective against cells in the S-phase, while vincristine and vinblastine are effective against cells in the mitotic phase.

We have found that the compounds of the invention as defined hereinafter are useful in combating abnormal cell proliferation; in particular the compounds have very good metaphase arresting ability which by virtue of its reversibility is of use for this purpose. A compound of formula I may possess a DNA synthesis inhibiting activity.

According to one aspect of the present invention, therefore, we provide compounds of general formula I,

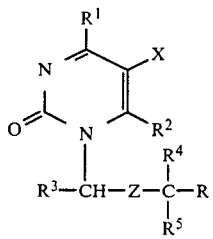

wherein
X represents a halogen atom, e.g. a fluorine, chlorine, bromine or iodine atom, or a trifluoromethyl group;
$R^1$ and $R^2$, independently represent a hydrogen atom or a lower alkyl group;
$R^3$, $R^4$ and $R^5$, which may be the same or different, each represent a hydrogen atom or a lower alkyl, lower alkenyl, lower alkynyl, lower alkanoyl, lower alkenoyl, $C_{7-16}$ aralkyl or $C_{6-10}$ aryl group or a 5-9 membered unsaturated or aromatic heterocyclic ring; one or both of $R^4$ and $R^5$ may also represent aroyl groups;
Z represents an oxygen atom or a sulfur atom or oxide thereof or a group $NR^6$ (wherein $R^6$ is as defined for R hereinafter or represents the group $COR^7$ in which $R^7$ represents a hydrogen atom or an aryl, heterocyclic, aralkyl, lower alkyl or lower alkoxy group optionally substituted by one or more substituents selected from halogen atoms, hydroxyl, amino, oxo or $C_{1-4}$ alkyl groups; and
R represents a $C_{6-10}$ carbocyclic aromatic group or a heterocyclic group containing a 5-9 membered unsaturated or aromatic heterocyclic ring which ring contains one or more heteroatoms selected from O, N and S and optionally carries a fused ring which carbocyclic or heterocyclic group may carry one or more $C_{1-4}$ alkyl or phenyl groups said group being optionally substituted by one or more substituents selected from halogen atoms, optionally substituted hydroxyl, optionally substituted amino, nitro, oxo, sulfonic acid and sulfonamido groups and thioether groups and oxides thereof; and where acid or basic groups are present, the salts thereof.

Certain compounds of formula I as hereinbefore defined and the salts thereof fall within the scope of the general disclosure of British Patent Specification No. 1,561,290, but there is no specific disclosure therein of any compound of the present invention. Moreover the compounds of the present invention possess especially good metaphase arresting ability compared with the compounds specifically disclosed in British Patent Specification No. 1,561,290.

The term "lower alkyl", "lower alkoxy", "lower alkenyl" or "lower alkynyl" as used herein in relation to a group or part of a group (i.e. moiety) preferably relates to such groups or moieties containing up to 6, more preferably up to 4, carbon atoms.

The terms "aryl" and "carbocyclic aromatic" as used herein in relation to a group or part of a group (i.e. moiety) preferably relate to a phenyl or naphthyl group, especially a phenyl group. Thus the term "aralkyl" as used herein conveniently relates to an aralkyl group in which the alkyl moiety contains 1-6 carbon atoms and the aryl moiety is a phenyl or naphthyl group. Preferred aralkyl groups contain from 7 to 10 carbon atoms e.g. a benzyl group.

The term "heterocyclic ring" as used herein preferably relates to a ring having 5 to 7 ring members especially 5 or 6 ring members and having one or more, advantageously one, two or three, heteroatoms selected from O, N and S. The "heterocyclic ring" is preferably an aromatic ring such as a thiophene, furan, thiadiazole or pyrimidine ring. The heterocyclic ring may have another ring fused to it which ring may be carbocyclic e.g. a benzene ring.

The term "optionally substituted hydroxyl" as used herein includes etherified and esterified hydroxy groups and thus includes for example alkoxy, aralkoxy and acyloxy as well as tetrahydropyranyloxy groups. The alkyl and aryl moieties of said alkoxy, aralkoxy and acyloxy groups may be as defined above. It will be appreciated that the term "acyl" as used herein includes the residue of an acid, such residues being not only the residues of carboxylic acids, but also the residues of for example phosphoric acids. Such acids may carry, for example, alkyl, aralkyl and aryl groups as defined above, which groups may for example carry hydroxy and/or carboxyl groups. The term "acyl" thus includes phosphate esters with alcohols and phenols, which alcohols and phenols may, if desired, carry further hydroxy substituents. Where hydroxy groups are present on adjacent carbon atoms a single substituent may link both oxygen atoms, as in the alkylidene e.g. methylidene group, to form an alkylidenedioxy e.g. methylenedioxy group. The term "optionally substituted hydroxyl" preferably relates to a $C_{1-4}$ alkoxy group.

The term "optionally substituted amino" as used herein includes amino groups carrying either one or two alkyl, aralkyl, aryl, lower alkanoyl, aralkanoyl, or aroyl groups, as well as cyclic imido groups derived from dibasic alkanoic, aralkanoic and aroic acids.

The term "thioether" group is used herein to include alkylthio, aralkylthio and arylthio groups, the alkyl, aralkyl and aryl moieties of which may be defined above. The term "thioether" group preferably relates to a $C_{1-4}$ alkylthio group especially a methylthio group.

The term "halogen" is used herein to mean fluorine, chlorine, bromine or iodine.

The term "lower alkanoyl" is used herein to include not only alkanoyl groups in which the carbonyl group carries a lower alkyl group having 1 to 6 carbon atoms but also formyl groups. The terms "aralkanoyl" and "aroyl" refer to aryl groups in which the carbonyl group carries an aralkyl or aryl group as defined above.

It will be appreciated that when an oxo group is situated on a carbon atom carrying an optionally substituted hydroxyl or optionally substituted amino group, these will together constitute a carbonyl function such as a carboxy, esterified carboxy or carboxamido group.

It will be appreciated that the substituents listed in the definition of R may be present on the carbocyclic aromatic group, on the unsaturated or aromatic heterocyclic group, on any fused rings or on any $C_{1-4}$ alkyl or phenyl substituents present on said carbocyclic aromatic or unsaturated or aromatic heterocyclic groups. Thus for example the group R may represent a carbocyclic or heterocyclic group substituted by a haloalkyl group such as a perfluoroalkyl e.g. a trifluoromethyl group, or by a hydroxyalkyl e.g. hydroxymethyl group.

$R^1$ and/or $R^2$ may represent a lower alkyl e.g. methyl group, but preferably $R^1$ and $R^2$ each represent a hydrogen atom.

The group $R^3$ may for example represent a lower alkyl group e.g. a methyl group, a lower alkanoyl group e.g. an acetyl group or advantageously a $C_{6-10}$ aryl group e.g. a phenyl group, but preferably $R^3$ represents a hydrogen atom.

The groups $R^4$ and $R^5$ may for example each represent a lower alkanoyl e.g. acetyl group, or a $C_{6-10}$ aryl group e.g. a phenyl group, but preferably represents a lower alkyl group e.g. a methyl group, or even more preferably hydrogen.

X preferably represents a halogen atom e.g. a chlorine atom.

Z may for example represent a sulphoxide or sulphone grouping or the group $NR^6$ in which $R^6$ represents a lower alkoxycarbonyl group e.g. an ethoxycarbonyl group or a lower alkanoyl group, e.g. a formyl or acetyl group, but Z advantageously represents an oxygen or sulphur atom or the group $N-COR^7$ in which $R^7$ represents a hydrogen atom or a $C_{1-6}$ alkoxy group. Z is preferably a sulphur atom, more preferably an oxygen atom.

R may for example represent a $C_{6-10}$ carbocyclic aromatic group e.g. a phenyl or naphthyl group or a 5- or 6-membered heterocyclic ring which group or ring is optionally substituted by one or more, (e.g. one, two or three) substituents selected from halogen, lower alkyl, lower alkoxy, lower haloalkyl, lower hydroxyalkyl, lower alkoxycarbonyl, nitro and lower alkanoyl. Thus for example R may represent an unsubstituted phenyl group or a phenyl group substituted by fluorine, chlorine, methyl, methoxy, trifluoromethyl, hydroxymethyl, methoxycarbonyl, nitro and/or acetyl. Substituents on the phenyl ring may be present, for example, in the 2-, 3- and/or 4-positions as in the 4-chlorophenyl, 3-trifluoromethylphenyl and 2-tolyl groups.

R preferably represents a $C_{6-10}$ carbocyclic aromatic group, e.g. a naphthyl but more preferably a phenyl group, or a 5- or 6-membered heterocyclic ring, e.g. a furyl, thienyl, pyrimidinyl or thiadiazolyl ring, which group or ring is optionally substituted by one or more substituents selected from halogen atoms and $C_{1-6}$ alkyl, $C_{1-6}$ alkoxy, $C_{1-6}$ haloalkyl, $C_{2-7}$ alkoxycarbonyl, $C_{1-6}$ hydroxyalkyl and $C_{1-6}$ alkylthio groups.

R more preferably represents a phenyl, naphthyl, furyl, thienyl, pyrimidinyl or thiadiazolyl group optionally substituted by one or more substituents selected from chlorine atoms and methyl, methoxy, trifluoromethyl, hydroxymethyl, methoxycarbonyl and methylthio groups.

Examples of the furyl, thienyl, pyrimidinyl and thiadiazolyl groups include fur-2-yl, thien-2-yl, pyrimidin-5-yl and 1,2,5-thiadiazolyl groups optionally substituted by one or more substituents selected from $C_{1-6}$ alkyl e.g. methyl groups and $C_{1-6}$ alkylthio e.g. methylthio groups. A particular group of this type is the 2-methylthio-4-methyl-pyrimidin-5-yl group.

Preferred compounds of the present invention based on their activity include compounds of formula I in which R represents an unsubstituted phenyl group or a phenyl group substituted by halogen, e.g. fluorine but especially chlorine, trifluoromethyl, lower alkyl e.g. methyl, lower alkoxy e.g. methoxy, or lower hydroxyalkyl e.g. hydroxymethyl; $R^1$, $R^2$, $R^3$, $R^4$ and $R^5$ each representing hydrogen and Z representing an oxygen or sulphur atom.

Particularly preferred compounds according to the invention are 1-(4-chlorobenzyloxy)methyl-5-chloropyrimidin-2-one and 1-(4-methoxybenzyloxy)-methyl-5-chloropyrimidin-2-one.

Where the compounds of formula I contain an acidic group, salts may be formed for example with alkali metal or alkaline earth metals, such salts including for example sodium, potassium, magnesium or calcium or ammonium (including substituted ammonium) salts. Compounds according to the invention carrying hydroxy or amino groups may also in general, possess enhanced water-solubility, the latter, or course, forming acid addition salts for example with mineral acids such as e.g. hydrochloric or sulphuric acid or organic acids such as e.g. acetic, tartaric or citric acid.

It will be appreciated that the compounds according to the invention, depending on the groups present, may exist in optical forms and all such forms as well as mixtures thereof are included within the scope of the invention.

It will be further appreciated that, for pharmaceutical use, the salts referred to above will be physiologically compatible but other salts may find use, for example in the preparation of compounds of general formula I and, where acidic or basic groups are present, their physiologically compatible salts.

The compounds of the invention are structurally quite simple and may be prepared by a variety of different processes. Reactions for the preparation of the six-membered pyrimidine ring system from ureas and three carbon atom components are well known in the art.

According to another aspect of the invention, therefore, we provide the following processes for the preparation of compounds of formula I as defined above:

Reaction (a)

A compound of formula II,

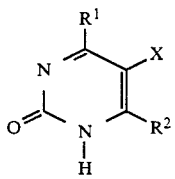
II (wherein X, $R^1$ and $R^2$ are as hereinbefore defined) or a salt thereof is reacted with an agent or agents serving to introduce the group $R^3$—CH—Z—$CRR^4R^5$. This agent may be of the formula

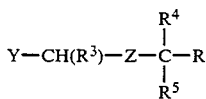
III

[wherein R, Z, $R^3$, $R^4$ and $R^5$ are as hereinbefore defined and Y represents a leaving atom or group e.g. a halogen atom, a hydroxy or mercapto group, a reactive ether or ester derivative or an amino or substituted amino group (as hereinbefore defined)]

A compound of formula III is advantageously used in which Y represents an iodine, bromine or chlorine atom or a hydrocarbonsulphonyl derivative such as a mesylate, brosylate or tosylate.

A compound of formula III may also, for example, be used in which Y represents a group

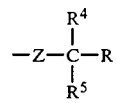

the group being chosen such that the compound of formula III is a symmetrical acetal or its sulfur or nitrogen analogue.

The reaction between the compounds of formula II and III is conveniently effected in the presence of a polar solvent such as an alkanol e.g. ethanol or dimethylformamide. The reaction may also conveniently be effected in the presence of a base, e.g. a tertiary organic base such as triethylamine conveniently in the presence of a halogenated hydrocarbon such as dichloromethane or an ether; or in the presence of an inorganic base e.g. an alkali metal hydroxide, such as potassium hydroxide, or an alkali metal carbonate, such as sodium carbonate, in the presence of a phase transfer catalyst such as benzyltrimethyl-ammonium chloride. Where a salt of the compound of formula (II) is used, an added base will not normally be required. Such a salt may, for example, be an alkali metal, e.g. sodium or potassium salt.

The group of formula

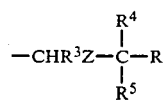

may also be introduced by a two stage reaction in which the compound of formula (II) is reacted with an O-silylating agent such as a bis(trialkylsilylamine) e.g. a bis(trimethylsilylamine) to form an O-silyl derivative, e.g. a trialkylsilyl ether such as a trimethylsilyl ether; followed by reaction with a compound of formula (III), preferably at an elevated temperature and conveniently in the absence of base. The reaction may also be effected, in the presence of a Lewis acid.

Where the reaction is effected at an elevated temperature the temperature is advantageously within the range 80° to 160° C. e.g. about 120° C. This two stage reaction involving O-silylation is especially advantageous since this process leads to selective N-alkylation thus substantially avoiding the formation of unwanted O-alkylated products which would otherwise significantly reduce the yield of the compound of formula I.

The reagent serving to introduce the group

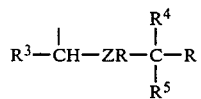

may, as indicated above, also be an alcohol of the formula

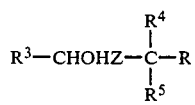

or a derivative thereof. It will be appreciated that the effective alkylating agent may be formed by loss of the hydroxyl group. In this case the reaction is carried out in the presence of a condensing agent such as an acetal of a $C_{1-5}$ dialkylformamide e.g. dimethyl formamide. The alkyl groups of the acetal are preferably neopentyl groups, thus dimethylformamide dineopentylacetal is preferred condensing agent.

Alternatively, the compound of formula III may be in the form of an acetal of a $C_{1-5}$ dialkylformamide carrying at least one acetal group derived from the alcohol

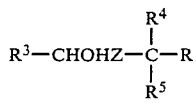

The compounds of formula (II) used as starting materials in reaction (a) may, for example, be prepared as described in our British Pat. No. 1,561,290. It is, however, difficult to prepare a 5-trifluoromethylpyrimidin-2-one of formula II by introduction of a trifluoromethyl group into the pyrimidin-2-one ring and it is thus preferred to prepare the 5-trifluoromethylpyrimidin-2-one of formula II by the methods described in our European Patent Application No. 82300106.0 (Publication Ser. No. 0,056,319).

The compounds of formula III may be prepared by conventional techniques, but in certain cases it may be particularly advantageous to prepare the compounds by methods analogous to methods (i)–(v) described in detail in our European Patent Application No. 82300106.0 (Publication Ser. No. 0056319) Thus the starting materials described in said processes (i)–(v) may be employed, the group R in European Patent Application No. 82300106.0 being replaced by the grouping:

as defined herein.

In addition to the methods described above for preparing the compounds of formula III we have found that compounds of formula III wherein Z represents an oxygen atom and Y represents a halogen atom may be prepared by halogenative cleavage of a compound of the formula:

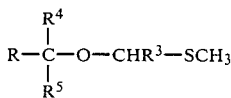    IV (wherein $R^3$, $R^4$, $R^5$ and R are as hereinbefore defined). A compound of formula IV may for example be used in which $R^3$ represents a hydrogen atom. The halogenative cleavage is preferably effected by the use of a halogenating agent such as sulfuryl chloride or sulfuryl bromide conveniently in the presence of a solvent such as a halogenated hydrocarbon e.g. dichloromethane, advantageously at ambient temperature.

The compounds of formula IV may preferably be first prepared by reacting a compound of the formula:

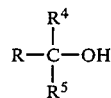    V (wherein R, $R^4$ and $R^5$ are as hereinbefore defined) or a salt thereof with a compound of formula:

$$CH_3S-CHR^3-Y \qquad VI$$

wherein $R^3$ is as hereinbefore defined and Y represents an atom or group removable as an anion e.g. a halogen atom such as a chlorine atom. The reaction is conveniently effected using a salt of the compound of formula V, for example an alkali metal salt e.g. the sodium salt. The reaction is conveniently effected in the presence of an iodide e.g. sodium iodide. The reaction is also conveniently effected in the presence of a solvent for example a polar solvent, e.g. an ether such as dimethoxyethane.

This process for the preparation of compounds of formula III in which Z is oxygen and Y represents a halogen atom is generally more advantageous than using the method based on method (v) described in European Patent application No. 82300106.0 because benzylates are stronger bases than phenolates and thus application of a method analogous to method (v) in the present case tends to result in side-reactions as a result of proton abstraction from the aryl thioether reagent which is avoided by the use of a corresponding methyl thioether. A further advantage of using a methyl thioether of formula IV is that on cleavage, the product (methanesulphenyl chloride) has a low boiling point (25° C./50 torr—H. Böhme and G. van Ham, Liebigs Ann. Chem. 617, 62(1958)) and may for example be removed with the solvent on distillation.

If desired, the compounds of formula IV, prepared by reaction of a compound of formula V or salt thereof with a compound of formula VI, may be reacted to convert one substituent to another prior to halogenative cleavage and/or reacted prior to halogenative cleavage to protect any atoms or groups which might be reactive or sensitive under the conditions of the halogenative cleavage. Thus for example a compound of formula IV in which R represents a phenyl group carrying carboxylic acid or ester substituent (e.g. a 4-ethoxycarbonylphenyl group) may be reduced to a hydroxymethyl substituent; for example with lithium aluminium hydride, prior to halogenative cleavage. In this case the hydroxymethyl substituent is advantageously protected by an appropriate protecting group, e.g. a tetrahydropyranyl group, prior to halogenative cleavage. The protecting group may, if desired, conveniently be removed after reaction of the compound of formula IV with the compound of formula II to form a compound of formula I.

Reaction (b)

Reaction of a compound of the formula:

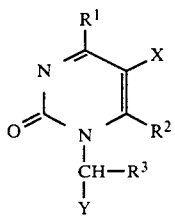
XV (wherein R¹, R², R³, X and Y are as hereinbefore defined) with an agent or agents serving to introduce the group

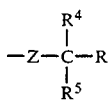

This agent may, for example, be a compound of the formula

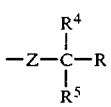

A compound of formula XV is preferably used in which Y represents a halogen atom, a hydroxyl group, a mercapto group, an activated ether or ether or an amino function. If desired Y may represent a group

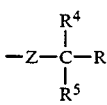

(Z, R⁴, R⁵ and R being as hereinbefore defined) in which case the reaction becomes an exchange reaction, the reaction conditions being chosen to promote the exchange.

The reaction is conveniently effected in the presence of an acid or a base.

The compounds of formula XV used as intermediates in this process may be prepared by methods analogous to those described in (a) above and (c) below.

The compound of formula XV may also for example be prepared by the halogenative cleavage of a compound of formula I in which Z represents a sulphur atom. A compound of formula I may for example be used in which R⁴ and R⁵ each represents a hydrogen atom. The compounds of formula XV may also be prepared by the halogenative cleavage of a compound corresponding to a compound of formula I but in which Z represents a sulphur atom and —CRR⁴R⁵ is replaced by an aryl group, preferably a chlorophenyl group. Such compounds may be prepared by a method analogous to that described in process (a) hereinbefore. The halogenative cleavage is preferably effected as described in process (v) for the preparation of compounds of formula III.

Reaction (c)

A compound of the formula:

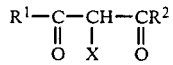
XVI (wherein X, R¹ and R² are as hereinbefore defined) or a functional derivative thereof such as an enol, acetal, enol ether, enol thioether, imine or enamine derivative, is reacted with a reagent serving to replace the oxo groups or functionally equivalent groups in formula XVI by a urea moiety

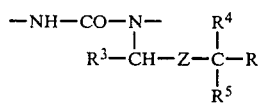

(wherein R, R³, R⁴, R⁵ and Z are as hereinbefore defined).

It will be appreciated that any reactive groups, e.g. oxo groups, present in R, R³, R⁴, R⁵ and/or Z which it is desired should not react may be protected by methods which are known from the literature, the protecting group(s) being removed following the cyclization reaction.

In one variation, the compound of formula XVI is reacted with a urea derivative of the formula:

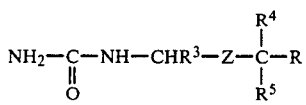
XVII (wherein Z, R, R³, R⁴ and R⁵ are as hereinbefore defined).

The reaction of the compounds of formula XVI and XVII may conveniently be effected in a solvent such as, for example, an alcohol, e.g. ethanol. The reaction proceeds at room temperature in the case where R¹ represents a hydrogen atom i.e. using a trifluoromethyl- or halo-malondialdehyde.

The urea reagent of formula XVII may, if desired, be replaced by a cyanamide of formula:

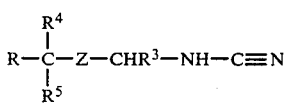

(wherein R, R³, R⁴ and R⁵ are as hereinbefore defined) which reacts to form an intermediate of formula:

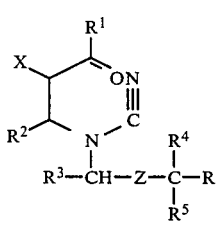
XVIII (wherein Z, R, R¹, R², R³, R⁴, R⁵ and X are as hereinbefore defined) which may readily be cyclised, for example, in the presence of water.

Reaction (d)

Oxidation of a compound of formula I as hereinbefore defined wherein Z represents a sulfur atom to form a compound of formula I in which Z represents an SO or SO$_2$ group.

The oxidation of the compound of formula I may be effected by any convenient method including the use of a peroxide or peracid oxidising system such as (1) hydrogen peroxide advantageously at ambient temperature; (2) m-chloroperbenzoic acid conveniently at a low temperature; (3) molybdenum peroxide conveniently in the presence of water and/or hexamethyl-phosphoramide but especially (4) hydrogen peroxide and selenium dioxide, for example under neutral conditions.

In general each oxidation method may be employed to prepare either the sulfone or the sulfoxide, the reaction conditions e.g. reaction time, temperature or excess of reagent being altered depending upon the desired product. Thus if it is desired to prepare the sulfone, longer reaction times, higher temperatures and/or excess of the oxidising agent may for example be used.

The above-mentioned oxidation to form sulfoxides and/or sulfones may, if desired, be effected using intermediates, which contain Z in the form of a sulfur atom, and which are of use in preparing the compounds of formula I as hereinbefore defined.

It will be appreciated that where a reaction is to be effected in which reactive or sensitive atoms or groups are present which it is desired should not react under the conditions of the reaction, such atoms or groups may be protected by any convenient protecting group which protecting group may be removed selectively after the reaction.

According to a further feature of the present invention there are provided pharmaceutical compositions comprising as active ingredient, at least one compound of formula I as hereinbefore defined or, where an acidic or basic group is present a physiologically compatible salt thereof in association with a pharmaceutical carrier or excipient.

For pharmaceutical administration the compounds of general formula I and, where acidic or basic groups are present, their physiologically compatible salts may be incorporated into the conventional preparations in either solid or liquid form.

The compositions may, for example, be presented in a form suitable for rectal, parenteral or topical administration. Preferred forms include, for example suspensions, suppositories, creams, ointments and lotions and solutions e.g. for injection or infusion or for ingestion by the gastro-intestinal tract. Solutions for injection are especially preferred.

The active ingredient may be incorporated in excipients customarily employed in pharmaceutical compositions such as, for example, talc, gum arabic, lactose, starch, magnesium stearate, cocoa butter, aqueous or non-agueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of active ingredient. Suitable dosage units for adults contain from 50 mg to 1.0 g of active ingredient. The dosage, which may be varied according to the compound used, the subject treated and the complaint concerned, may, for example, be from 0.25 to 7.0 g in a day in adults.

It will normally be necessary to have a knowledge of cell cycle kinetics (for example as determined by cytofluorography) of both the normal and abnormal cells and to prepare time schedules which indicate how long after administration of the drug the majority of the abnormal cells will reach a phase which is susceptible to attack by a chosen cytotoxic drug while the majority of normal cells are in a nonsusceptible phase. These periods will naturally differ widely. Suitable cytotoxic drugs include cytosine arabinoside and hydroxyurea which are cytotoxic against cells in the S-phase. Since the S-phase is generally longer than the other phases, it is easier to find appropriate time schedules when using cytotoxic drugs in this phase.

The following Preparations illustrate the production of starting materials for use in the processes of the present invention. The Examples, which are given by way of illustration only, exemplify processes of the present invention.

PREPARATIONS 1-8

Chloromethyl ethers for use as starting materials in the Examples (a) O,S-Acetals of the formula: RR$^4$R$^5$C—O—CH$_2$—SCH$_3$ were prepared by reaction of chloromethyl methyl sulphide in the presence of sodium iodide and the sodium salt of the benzylic alcohol in dimethoxyethane (DME) according to the procedure described by E. J. Corey and M. C. Bock in Tetrahedron Letters 38, 3269(1975).

The yields, physical properties and analytical data are set out in Table 1.

(b) Chloromethyl ethers of the formula RR$^4$R$^5$C—O—CH$_2$Cl for use as starting materials in the Examples were prepared by the dropwise addition of sulfuryl chloride (20 mmol) in dry dichloromethane (40 ml) over a period of 15 minutes at room temperature to a solution of the O,S-acetal (20 mmol) in dry dichloromethane (60 ml). The mixture was stirred for 30 min. before the solvent and the methanesulfenyl chloride was evaporated together at reduced pressure, and finally the residue was distilled. The yields, physical properties and analytical data are given in Table 2.

TABLE 1

| | | | | | | O,S—acetals | | |
|---|---|---|---|---|---|---|---|---|
| Preparation No. | R | R$^4$ | R$^5$ | Yield [%]$^a$ | b.p./torr [°C.] | Molecular formula$^b$ or Lit. b.p./torr [°C.] | $^1$H—N.M.R —OCH$_2$— | (CDCl$_3$) δ [ppm] other signals |
| 1a | C$_6$H$_5$ | H | H | 56 | 46–48°/0.1 | C$_9$H$_{12}$OS (168.3) | 4.62 | 2.19(s,3H); 4.69(s,2H) 7.34(s,5H) |
| 2a | C$_6$H$_5$ | H | CH$_3$ | 61 | 45–48°/0.01 | C$_{10}$H$_{14}$OS (182.3) | 4.35 4.63 | 1.49(d,J=7H$_2$,3H); 2.13(s,3H) 4.85(q,J=7H$_2$,1H); 7.23(s,5H) |
| 3a | 2-H$_3$C—C$_6$H$_4$— | H | H | 70 | 55–65°/0.01 | C$_{10}$H$_{14}$OS (182.3) | 4.56 | 2.15(s,3H); 2.33(s,3H); 4.63 (s,2H); 7.07(s,4H) |
| 4a | 4-H$_3$CO—C$_6$H$_4$— | H | H | 80 | 78–84° C./0.01 | C$_{10}$H$_{14}$O$_2$S (198.3) | 4.49 | 2.13(s,3H); 3.76(s,3H); 4.60 (s,2H); 6.6–7.3 (m,4H) |

TABLE 1-continued

O,S—acetals

| Preparation No. | R | $R^4$ | $R^5$ | Yield [%][a] | b.p./torr [°C.] | Molecular formula[b] or Lit. b.p./torr [°C.] | $^1$H—N.M.R —OCH$_2$— | (CDCl$_3$) δ [ppm] other signals |
|---|---|---|---|---|---|---|---|---|
| 5a | 4-Cl—C$_6$H$_4$ | H | H | 55 | 68–75°/0.01 | C$_9$H$_{11}$ClOS (202.7) | 4.53 | 2.14(s,3H); 4.63(s,2H) 7.24(s,4H) |
| 6a | 3-F$_3$C—C$_6$H$_4$— | H | H | 68 | 48°/0.1 | C$_{10}$H$_{11}$F$_3$OS (236.3) | 4.61 | 2.15(s,3H); 4.67(s,2H) 7.3–7.6(m,4H) |
| 7a | 2-furyl | H | H | 77 | 45–48°/0.01 | C$_7$H$_{10}$O$_2$S (158.2) | 4.56 | 2.13(s,3H); 4.63(s,2H) 6.2–6.3(m,2H); 7.2–7.3(m,1H) |
| 8a | 2-thienyl | H | H | 71 | 60–64°/0.01 | C$_7$H$_{10}$OS$_2$ (174.3) | 4.63 | 2.13(s,3H); 4.73(s,2H) 6.8–7.2(m,3H) |

TABLE 2

Chloromethyl ethers

| Preparation No. | No. of Example in which product is used | R | $R^4$ | $R^5$ | Yield [%][a] | b.p./torr [°C.] | Molecular formula[b] or Lit. b.p./torr [°C.] | $^1$H—N.M.R —OCH$_2$— | (CDCl$_3$) δ [ppm] other signals |
|---|---|---|---|---|---|---|---|---|---|
| 1b | 1,13,16 | C$_6$H$_5$ | H | H | 83 | 40°/0.1 | 53–56°/1.5[f] | 5.44 | 4.68(s.2H); 7.28(s.5H) |
| 2b | 11 | C$_6$H$_5$ | H | CH$_3$ | 94 | 34–36°/0.01 | C$_9$H$_{11}$ClO (170.6) | 5.13 5.46 | 1.50(d.J=7Hz,3H); 4.90 (q.J=7Hz,1H); 7.23(2.5H) |
| 3b | 3 | 2-H$_3$C—C$_6$H$_4$— | H | H | 95 | 48–52°/0.01 | 112–113°/10[g] | 5.44 | 2.32(s.3H); 4.70(s.2H) 7.09(s.4H) |
| 4b | 4 | 4-H$_3$CO—C$_6$H$_4$— | H | H | 70 | 67–77°/0.01 | C$_9$H$_{11}$ClO$_2$ (186.6) | 5.41 | 3.78(s.3H); 4.63(s.2H) 6.7–7.3(m.4H) |
| 5b | 2,12,14,15 | 4-Cl—C$_6$H$_4$— | H | H | 95 | 55–58°/0.01 | 106–108°/5[h] | 5.44 | 4.66(s.2H); (s.4H) |
| 6b | 5 | 3-F$_3$C—C$_6$H$_4$ | H | H | 89 | 48–52°/0.1 | C$_9$H$_8$ClF$_3$O | 5.47 | 4.75(s.2H); 7.2–7.6(m.4H) |
| 7b | 6 | 2-furyl | H | H | 71 | 20–22°/0.01 | [e] | 5.40 | 4.64(s.2H); 6.2–6.4(m.2H) 7.3–7.4(m.1H) |
| 8b | 7 | 2-thienyl | H | H | 95 | 34–36°/0.01 | [e] | 5.40 | 4.83(s.2H); 6.7–7.3(m,3H) |

[a]Yield of isolated product
[b]Satisfactory microanalyses obtained
[c]ABq, J gem = 11 Hz
[d]ABq, J gem = 6 Hz
[e]Product not stable
[f]see D. S. Conner, G. W. Klein and G. N. Taylor; Org. Synthesis; 52 16 (1972)
[g]see S. Mamedov, E. G. Dzhagupova and M. A. Avanesyan; Zh. Obsh. Khim 33. 836 (1963)
[h]see S. Mamedov, Z. T. Eminova, A. R. Rzaev and M. A. Avanesyan; Chem. Abstr. 68, 39252n (1968)

PREPARATION 9

1-(Chloromethyloxymethyl)naphthalene (a) Methylthiomethyl 1-naphthylmethyl ether was prepared by the reaction of chloromethyl methyl sulfide with the sodium salt of naphthalene-1-methanol in DME in the presence of sodium iodide as described for analogous reactions by E. J. Corey and M. C. Bock in Tetrahedron letters 38 3269(1975); yield 50%, b.p. 105°–115° C./0.01 mmHg. $^1$H NMR (CDCl$_3$): δ2.17 (Me), 4.70 (CH$_2$S), 5.01 (CH$_2$Naph), 7.1–8.2 (Naph).

(b) 1-Chloromethyloxymethyl)naphthalene Sulfuryl chloride (12 mmol) in dry dichloromethane (20 mmol) was added dropwise with stirring to a solution of methylthiomethyl 1-naphthylmethyl ether (12 mmol) in dry dichloromethane (40 ml) at room temperature. After stirring for 30 min the solvent and methanesulfenyl chloride formed in the reaction were distilled off at reduced pressure. The residual material was used for alkylation without further purification. $^1$H NMR (CDCl$_3$): δ5.13 (CH$_2$), 5.47 (CH$_2$Cl), 7.2–8.3 (Naph).

PREPARATION 10

3-(Chloromethyloxymethyl)-1,2,5-thiadiazole (a) 3-(Methylthiomethyloxy)methyl-1,2,5-thiadiazole was prepared from 3-hydroxymethyl-1,2,5-thiadiazole (see D. M. Mulway and L. W. Weinstock; J. Heterocycl. Chem. 4, 445(1967)) by the general procedure described by E. J. Corey and M. C. Bock in Tetrahedron Letters 38 3269(1975).

(b) 3-(Chloromethyloxymethyl)-1,2,5-thiadiazole Sulfuryl chloride (0.24 mmol) in dry dichloromethane (0.5 ml) was added dropwise over a period of 3 minutes at 0° C. to a solution of 3-(Methylthiomethyloxy)methyl-1,2,5-thiadiazole (0.24 mmol) in dry dichloromethane (1.5 ml). The mixture was stirred at 0° C. for 5 minutes and at room temperature for 10 minutes before the solution was evaporated at reduced pressure. The crude product (30 mg, 75%) was used for alkylation in Example 9 without any further purification.

PREPARATION 11

2-Methylthio-4-methyl-5-(chloromethyloxymethyl)-pyrimidine (a) 2-Methylthio-4-methyl-5-hydroxymethylpyrimidine A solution of 2-methylthio-4-methyl-5-formylpyrimidine (see T. Benneche and K. Undheim; Acta Chem. Scand. B 36, 529(1982)) (2 mmol) in ether (10 ml) was added dropwise over 5 minutes at 0° C. to a suspension of lithium aluminium hydride (1.2 mmol) in ether (10 ml). The mixture was stirred at 0° C. for 1 hour before water (10 ml) was added. The layers were separated and the aqueous phase extracted with boiling CH$_2$Cl$_2$ (3×15 ml). The combined organic phase was dried (MgSO$_4$) and evaporated. Yield: 0.23 g (68%), m.p. 49° C. (pet. ether). Lit. m.p. 48.0°–48.5° C. (pet. ether). (see R. S. Shadbolt and T. L. V. Ulbricht, J. Chem. Soc. C, 1968,733).

(b) 2-Methylthio-4-methyl-5-(methylthiomethyloxy)-methylpyrimidine was prepared from 2-methylthio-4- methyl-5-hydroxymethylpyrimidine by the general procedure described by E. J. Corey and M. C. Bock in Tetrahedron Letters, 38, 3269(1975); yield: 46%. Oil. $^1$H NMR (CDCl$_3$): δ2.15 (CH$_3$), 2.45 (CH$_3$), 2.50 (CH$_3$), 4.52 (—CH$_2$), 4.66 (CH$_2$), 8.22 (H-6).

(c) 2-Methylthio-4-methyl-5-(chloromethyloxymethyl)pyrimidine Sulfuryl chloride (2.8 mmol) in dry dichloromethane (5 ml) was added dropwise over 15 minutes at −3° C. to a solution of 2-methylthio-4-methyl-5-(methylthiomethyloxy)methylpyrimidine (2.8 mmol) in dry dichloromethane (10 ml). The mixture was stirred at −3° C. for 10 minutes before the solution was evaporated at reduced pressure. The crude product (0.60 g, 98%) was used for alkylation in Example 10 without any further purification. $^1$H NMR (CDCl$_3$): δ2.64 (4-CH$_3$ and SCH$_3$), 4.73 (CH$_2$), 5.50 (CH$_2$), 8.47 (H-6).

PREPARATION 12

Chloromethyl 4-(tetrahydropyran-2-yloxymethyl)benzyl ether (a) 4-(Methyloxycarbonyl)benzyl methylthiomethyl ether was prepared by the reaction of chloromethyl methyl sulphide with the sodium salt of methyl 4-hydroxymethylbenzoate (see G. D. Brindell, L. D. Lillwitz, J. P. Wuskell and A. P. Dunlop, Ind. Eng. Chem. Prod. Res. Dev. 15, 83(1976) in dimethoxyethane in the presence of sodium iodide as described for analogous reactions in E. J. Corey and M. C. Bock, Tetrahedron Letters 38 3269 (1975); yield 75%, b.p. 110°–120° C./0.01 mmHg. $^1$H NMR (CDCl$_3$): δ2.17 (SMe) 3.92 (OMe), 4.67 (CH$_2$), 4.70 (CH$_2$), 7.2–8.2 (Ph).

(b) 4-(Hydroxymethyl)benzyl methylthiomethyl ether 4-(Methoxycarbonyl)benzyl methylthiomethyl ether (45 mmol) was added with stirring to lithium aluminium hydride (26 mmol) in ether (75 ml) at a rate which produced gentle reflux. The mixture was stirred for 10 minutes after all the ester had been added before the reaction was stopped by dropwise addition of water and the mixture neutralized with 10% H$_2$SO$_4$ with ice cooling. The ether phase was collected, the aqueous phase extracted with ether (twice), the combined ether solutions washed with water and the dried (MgSO$_4$) solution evaporated; yield of title compound 8.43 g (95%), m.p. 54° C. $^1$H NMR (CDCl$_3$): δ2.18 (Me), 4.57 (CH$_2$), 4.62 (CH$_2$), 4.67 (CH$_2$), 7.27 (Ph).

(c) Methylthiomethyl 4-(tetrahydropyran-2-yloxymethyl)benzyl ether p-Toluenesulfonic acid (0.1 mmol) was added to a solution of 4-(hydroxymethyl)benzyl methylthiomethyl ether (21 mmol) and 2,3-dihydropyran (40 mmol) in dichloromethane (40 ml) and the solution heated under reflux for 1 h. The cold solution was filtered through a short column of neutral alumina and the solvent distilled off at reduced pressure; the residual material was the title compound, yield 3.97 g (70%). The chromatographically homogenous material was used in the subsequent reaction without any further purification. $^1$H NMR (CDCl$_3$): δ1.3–1.8 (6H, m, THP), 2.17 (Me), 3.3–4.3 (2H, m) 4.5–4.8 (3CH$_2$, CH), 7.34 (Ph), (d) Chloromethyl 4-(tetrahydropyran-2-yloxymethyl)benzyl ether V Sulfuryl chloride (4.7 mmol) in dry dichloromethane (20 mmol) was added dropwise with stirring over 6 min to a solution of methylthiomethyl 4-(tetrahydropyran-2-yloxymethyl)benzyl ether (4.7 mmol) in dry dichloromethane (14 ml) at −78° C. The temperature was kept at −78 ° C. for 25 min before cyclohexene (0.39 g, 4.7 mmol) in dichloromethane (10 ml) was added dropwise. The reaction mixture was allowed to reach room temperature (30 min), the solvent evaporated and the sulfenyl chloride trapped as 2-methylthio-1-chlorohexane distilled off (b.p. 40° C./0.01 mmHg). The residue, the title compound, was used directly in the ensuing alkylation without any further purification; yield almost quantitative. $^1$H NMR (CDCl$_3$): δ1.4–1.9 (6H, THP), 3.3–4.2 (2H, m), 4.5–4.9 (2CH$_2$, CH), 5.45 (CH$_2$Cl), 7.31 (Ph).

PREPARATION 13

Chloromethyl 4-methyloxycarbonylbenzyl ether

Sulfuryl chloride (8.8 mmol) in dichloromethane (15 ml) was added dropwise with stirring to a solution of 4-(methoxycarbonyl)benzyl methylthiomethyl ether (see Preparation 12a) (8.8 mmol) in dichloromethane (30 ml) at room temperature. The mixture was stirred for 30 min before the solvent and the methanesulfenyl chloride (formed in the reaction) was distilled off at reduced pres-sure. The residue, the title compound, was used directly in the ensuing alkylation without any further purification; yield 1.15 g (almost quantitative). $^1$H NMR (CDCl$_3$): δ3.93 (Me), 4.80 (CH$_2$), 5.54 (CH$_2$Cl), 7.2–8.2 (Ph).

EXAMPLE 1

1-(Benzyloxy)methyl-5-chloropyrimidin-2-one

A mixture of 5-chloropyrimidin-2-one hydrochloride (10 mmol) and triethylamine (20 mmol) in dichloromethane (50 ml) were stirred together until all the solid material had dissolved, before a solution of chloromethyl benzyl ether (see Preparation 1a and 1b) (10 mmol) in dichloromethane (10 ml) was added with stirring at room temperature. The mixture was stirred for 3 hours at room temperature before the solvent was distilled off. The residue was triturated with water (40 ml), extracted into chloroform (3×40 ml) and the dried (MgSO$_4$) solution evaporated; yield 2.40 g (96%). The product was purified by trituration with ether and had m.p. 125° C. (acetone). $^1$H NMR (CDCl$_3$): δ4.68 (CH$_2$Ph), 5.32 (CH$_2$O), 7.30 (Ph), 7.72 and 8.48 (H-4, H-6, J 3 Hz).

EXAMPLE 2

1-(4-Chlorobenzyloxy)methyl-5-chloropyrimidin-2-one was prepared as described in Example 1 from 4-chlorobenzyl chloromethyl ether (see Preparation 5a and 5b or Chem Abstr. 68 39252n (1968)) (15 mmol) and 5-chloropyrimidin-2-one hydrochloride (15 mmol) by allowing the reaction to proceed for 24 hours at room temperature. The title compound had m.p. 147° C. (acetone). $^1$H NMR (CDCl$_3$): δ4.63 (CH$_2$ Ph), 5.32 (CH$_2$O), 7.25 (Ph), 7.78 and 8.47 (H-4, H-6, J 3 Hz).
IR(KBr): 1665 cm$^{-1}$ (CO).

EXAMPLE 3

1-(2-Methylbenzyloxy)methyl-5-chloropyrimidin-2-one

A solution of chloromethyl 2-methylbenzyl ether (see Preparation 3a and 3b) (10 mmol) in dichloromethane (20 ml) was added dropwise with stirring to a solution of 5-chloropyrimidin-2-one hydrochloride (10 mmol) and triethylamine (20 mmol) in dichloromethane (80 ml). The reaction mixture was stirred for 2 hours at room temperature. It was then washed with water and the dried (MgSO$_4$) solution evaporated to yield a crude mixture (2.55 g, 96%) which was purified by trituration with ether. The yield of the title compound was 1.33 g (50%), m.p. 88° C. $^1$H NMR (CDCl$_3$): δ2.26 (Me), 4.63 (CH$_2$-Ph), 5.30 (CH$_2$O), 7.00 (Ph), 7.60 and 8.37 (H-4, H-6, J 4 Hz). IR(KBr): 1660 cm$^{-1}$ (CO).

EXAMPLE 4

1-(4-Methoxybenzyloxy)methyl-5-chloropyrimidin-2-one was prepared as described in Example 3 from chloromethyl 4-methoxybenzyl ether (see Preparation 4a and 4b) (10 mmol) and 5-chloropyrimidin-2-one (10 mmol) in 52% yield (1.45 g), m.p. 118° C. $^1$H NMR (CDCl$_3$): δ3.77 (OMe), 4.57 (CH$_2$Ph), 5.27 (CH$_2$O), 6.6–7.3 (Ph), 7.63 and 8.35 (H-4, H-6, J 4 Hz). IR(KBr): 1670 cm$^1$ (CO).

EXAMPLE 5

1-(3-Trifluoromethylbenzyloxy)methyl-5-chloropyrimidin-2-one was prepared as described in Example 3 from chloromethyl 3-trifluoromethyl-benzyl ether (see Preparation 6a and 6b) (10 mmol) and 5-chloropyrimidin-2-one hydrochloride (10 mmol) in 52%. (1.66 g) yield, m.p. 95° C. $^1$H NMR (CDCl$_3$): δ4.77 (CH$_2$Ph), 5.42 (CH$_2$O), 7.3–7.7 (Ph), 7.82 and 8.55 (H-4, H-6, J 4 Hz). IR(KBr): 1660 cm$^{-1}$ (CO).

EXAMPLE 6

1-(2-Furfuryloxy)methyl-5-chloropyrimidin-2-one was prepared as described in Example 3 from 2-(chloromethyloxymethyl)furan (see preparation 7a and 7b) (10 mmol) and 5-chloropyrimidin-2-one hydrochloride (10 mmol) in 54% yield (1.30 g), m.p. 95° C. $^1$H NMR (CDCl$_3$): δ4.61 (CH$_2$ Fur.), 5.30 (OCH$_2$), 6.2–6.4 and 7.2–7.3 (3H-Fur.), 7.73 and 8.34 (H-4, H-6, J 4 Hz). IR(KBr): 1660 cm$^{-1}$ (CO).

EXAMPLE 7

1-(2-Thenyloxy)methyl-5-chloropyrimidin-2-one was prepared as described in Example 3 from 2-(chloromethyloxymethyl)thiophene (see Preparation 8a and 8b) (10 mmol) and 5-chloropyrimidin-2-one hydrochloride (10 mmol) in 57%. yield (1.45 g), m.p. 132° C. $^1$H NMR (CDCl$_3$): δ4.80 (CH$_2$Thioph.), 5.28 (CH$_2$O), 6.7–7.2 (3H-Thioph.), 7.63 and 8.35 (H-4, H-6, J 4 Hz). IR(KBr): 1660 cm$^{-1}$ (CO).

EXAMPLE 8

1-(1-Naphthylmethyloxy)methyl-5-chloropyrimidin-2-one was prepared as described in Example 3 from 1-(chloromethyloxymethyl)naphthalene (see Preparation 9) (10 mmol) and 5-chloropyrimidin-2-one hydrochloride (10 mmol). The crude product mixture (96% yield) was purified by chromotography on alumina using dichloromethane to develop the column; yield 33% (1.00 g) of the non-crystalline title compound. $^1$H NMR (CDCl$_3$): δ5.05 (CH$_2$Naph.), 5.26 (CH$_2$O), 7.2–8.0 'H-4 and Naph.), 8.20 (H-6, J 4 Hz).

MS[70 eV; m/z (% rel.int.)]: 300(0.1, M), 170(5), 169(10), 157(4), 156(3), 155(14), 147(4), 144(100), 139(23).

EXAMPLE 9

1-(1,2,5-Thiadiazol-3-yl methyloxy)methyl-5-chloropyrimidin-2-one 3-(Chloromethyl)oxymethyl-1,2,5-thiadiazole (see Preparation 10) (0.18 mmol) in dichloromethane (1 ml) was added dropwise with stirring at room temperature to a solution of 5-chloropyrimidin-2-one hydrochloride (18 mmol) and triethylamine (0.36 mmol) in dichloromethane (3 ml). The mixture was stirred for 1½ hours at 40° C. before the solvent was distilled off. The residue was triturated with water, extracted into chloroform and the dried (MgSO$_4$) solution evaporated. Trituration of the residue with ether left the title compound in 20% (11 mg) yield, m.p. 106° C. $^1$H NMR (CDCl$_3$): δ5.00 (CH$_2$Het), 5.40 (OCH$_2$), 7.73 and 8.47 (H-4, H-6, J 3 Hz), 8.50 (H-3$^1$).

EXAMPLE 10

1-[(2-Methylthio-4-methylpyrimidin-5-yl)methyloxy]-methyl-5-chloropyrimidin-2-one 2-Methylthio-4-methyl-5-(chloromethyloxymethyl)-pyrimidine (see Preparation 11) (2.7 mmol) in dichloromethane (5 ml) was added dropwise with stirring at room temperature to a solution of 5-chloropyrimidin-2-one hydrochloride (2.7 mmol) and triethylamine in dichloromethane (0.76 ml). The mixture was stirred for 24 hours at room temperature before the solvent was distilled off. The residue was triturated with water, extracted into chloroform and the dried (MgSO$_4$) solution evaporated. yield 0.55 g (65%). $^1$H NMR (CDCl$_3$): δ2.42 (4-Me), 2.55 (SMe), 4.65 (CH$_2$Pyr), 5.32 (CH$_2$O), 7.80 and 8.42 (H-4, H-6, J 3 Hz), 8.20 (H-6').

EXAMPLE 11

1-(α-Phenylethyloxy)methyl-5-chloropyrimidin-2-one was prepared as described in Example 3 from benzyl 1-chloroethyl ether (see Preparation 2a and 2b) (10 mmol) and 5-chloropyrimidin-2-one (10 mmol) in 58%. (1.53 g) yield, m.p. 139° C. $^1$H NMR (CDCl$_3$): δ1.50 and 4.63 (CH$_3$—CH, J 6 Hz), 5.18 (CH$_2$), 7.0–7.3 (Ph), 7.57 and 8.27 (H-4, H-6, J 4 Hz). IR (KBr): 1670 cm$^{-1}$ (CO).

EXAMPLE 12

1-(4-Chlorobenzyloxy)methyl-5-fluoropyrimidin-2-one was prepared as described in Example 3 from 4-chlorobenzyl chloromethyl ether (see Preparation 5a and 5b) (4 mmol) and 5-fluoropyrimidin-2-one (4 mmol) by allowing the reaction to proceed for 6 hours at room temperature; yield 70% (0.75 g), m.p. 103° C. $^1$H NMR (CDCl$_3$): δ4.62 (CH$_2$Ph), 5.30 (CH$_2$N), 7.17 (Ph), 7.63 and 8.53 (H-4, H-6). IR(KBr): 1670 cm$^{-1}$ (CO).

EXAMPLE 13

1-(Benzyloxy)methyl-5-bromopyrimidin-2-one was prepared as described in Example 3 from benzyl chloromethyl ether (see Preparation 1a and 1b) (4 mmol) and 5-bromopyrimidin-2-one by allowing the reaction to proceed for 20 hours at room temperature; yield 29% (0.34 g), m.p. 169° C. $^1$H NMR (CDCl$_3$): δ4.65 (CH$_2$Ph), 5.30 (CH$_2$O), 7.18 (Ph), 7.78 and 8.40 (H-4, H-6, J 4 Hz). IR(KBr): 1670 cm$^{-1}$ (CO).

EXAMPLE 14

1-(4-Chlorobenzyloxy)methyl-5-iodopyrimidin-2-one

4-Chlorobenzyl chloromethyl ether (see Preparation 5a and 5b) (3.3 mmol) was added to the potassium salt of 5-iodopyrimidin-2-one (3.3 mmol) in DMF (40 ml) and the mixture stirred at 50° C. for 2 hours. The solvent was then distilled off at reduced pressure, the residue triturated with water (50 ml) and extracted into chloroform. Evaporation of the dried (MgSO$_4$) solution gave the crude product (1.05 g, 81%). Trituration of the product with ether left the title compound; yield 0.58 g (45%), m.p. 168° C. (acetone). $^1$H NMR (CDCl$_3$): δ4.66 (CH$_2$Ph), 5.35 (CH$_2$O), 7.31 (Ph), 7.71 and 8.61 (H-4, H-6, J 3 Hz).

EXAMPLE 15

1-(4-Chlorobenzyloxy)methyl-5-trifluoromethylpyrimidin-2-one

Triethylamine (1 mmol) was added to a mixture of 5-trifluoromethyl pyrimidin-2-one (see Preparation 11 of European Patent Publication Ser. No. 0 056 319) (1 mmol) in dichloromethane (10 ml) and the solution stirred for 5 minutes before 4-chlorobenzyl chloromethyl ether (see Preparation 5a and 5b) (1 mmol) in dichloromethane (2 ml) was added. The mixture was stirred at room temperature overnight and at 40° C. for 3 hours before the solvent was distilled off and the residue triturated with water. The product was extracted into chloroform, dried (MgSO$_4$) and evaporated. The residue was washed with ether and dried; yield 91%, m.p. 120° C. $^1$H NMR (CDCl$_3$): δ4.64 (CH$_2$Ph), 5.38 (NCH$_2$), 7.24 (Ph), 8.11 (H-4, J 3 Hz), 8.74 (H-6, J 3 Hz). IR (KBr): 1680 cm$^{-1}$ (CO).

EXAMPLE 16

1-(Benzylthio)methyl-5-chloropyrimidin-2-one

Potassium tert.-butoxide (20 mmol) in DMF (60 ml) was added to a solution of 5-chloropyrimidin-2-one hydrochloride (10 mmol) in DMF (60 ml) and the mixture stirred at room temperature for 10 minutes before benzyl chloromethylthioether (see Preparation 1a and 1b or L. A. Paquette, L. S. Wittenbrook and K. Schreiber, J. Org. Chem. 33, 1080 (1968)) (10 mmol) was added. The resultant mixture was stirred at 70° C. for 2 hours before the solvent was distilled off at reduced pressure and the residue triturated with water. The residual crude product (2.53 g, 95%) was triturated with ether to leave the title compound in 36% (0.96 g) yield, m.p. 186° C. $^1$H NMR (CDCl$_3$): δ3.84 (CH$_2$Ph), 4.90 (CH$_2$S), 7.20 (Ph), 7.48 and 8.30 (H-4, H-6, J 4 Hz). IR(KBr): 1660 cm$^{-1}$ (CO).

EXAMPLE 17

1-(N-Benzyl-N-ethoxycarbonylamino)methyl-5-chloropyrimidin-2-one

N-Chloromethyl-N-ethoxycarbonylbenzylamine (see German Offenlegungsschrift No. 2,119,518) (10 mmol) in dichloromethane (20 ml) was added dropwise with stirring to a solution of 5-chloropyrimidin-2-one hydrochloride (20 mmol) in dichloromethane (80 ml). The reaction mixture was stirred at room temperature for 2 hours, extracted with water, the solution dried (MgSO$_4$) and evaporated. The residual crude product (yield 80%, 2.57 g) was triturated with ether to leave the title compound in 53% yield (1.70 g), m.p. 143° C. $^1$H NMR (CDCl$_3$): δ1.31 and 4.22 (EtO), 4.73 (CH$_2$Ph), 5.23 (CH$_2$N), 7.20 (Ph), 8.03 and 8.38 (H-4, H-6, J 4 Hz). IR(KBr): 1670 cm$^{-1}$ (CO), 1720 (CO-carbamate).

EXAMPLE 18

1-[α-(Benzylthio)benzyl]-5-chloropyrimidin-2-one

α-Chlorobenzyl benzyl sulphide (see R. H. Mitchell, Tetrahedron Letters 44, 4395 (1973) (4 mmol) in CH$_2$Cl$_2$ (10 ml) was added dropwise over a period of 5 minutes at 0° C. to a mixture of 5-chloropyrimidin-2-one hydrochloride (4 mmol) and triethylamine (8 mmol) in CH$_2$Cl$_2$ (30 ml). The mixture was stirred for 3 hours at room temperature and ½ hour at 40° C. before chloroform (20 ml) was added and the solution washed with water (3 times). The dried (MgSO$_4$) solution was evaporated, ether added to the crude product and the insoluble product collected. Yield 0.35 g (26%), m.p. 118° C. $^1$H-NMR (CDCl$_3$): δ(CH$_2$) 7.12 (—CH—), 7.27 (Ph), 7.33 (Ph), 8.12 (H-4, d, J 3 Hz)), 8.30 (H-6, d, J 3 Hz).

EXAMPLE 19

1-[4-(Tetrahydropyran-2-yloxymethyl)benzyloxy]methyl-5-chloropyrimidin-2-one Chloromethyl 4-(tetrahydropyran-2-yloxymethyl)benzyl ether (see Preparation 12) (4.7 mmol) in dichloromethane (40 ml) was added dropwise with stirring to a solution of 5-chloropyrimidin-2-one (4.7 mmol) and triethylamine (4.7 mmol) in dichloromethane (10 ml). The mixture was stirred at room temperature for 2 hours and was then washed with water, the organic solution dried (MgSO$_4$) and the solvent distilled off to yield a crude product in 89% yield (1.53 g), which was extracted with ether and the residual material purified on neutral alumina eluting with dichloromethane and subsequently with 10% MeOH in dichloromethane; yield 0.42 g (26%) of the non-crystalline title compound. $^1$H NMR (CDCl$_3$): δ1.4–2.0 (6H, m, THP), 3.3–4.3 (2H, m), 4.5–4.9 (2CH$_2$, CH), 5.37 (NCH$_2$), 7.38 (Ph), 7.88 and 8.53 (H-4, H-6, J 4 Hz).

EXAMPLE 20

1-[4-(Hydroxymethyl)benzyloxy]methyl-5-chloropyrimidin-2-one

Dowex 50W-X8 ion exchanger in the acid form (0.29 g) was added to a solution of 1-[4-(tetrahydropyran-2-yloxymethyl)benzyloxy]methyl-5-chloropyrimidin-2-one (see Example 19) (1.2 mmol) in methanol (2 ml) and chloroform (0.5 ml) and the mixture stirred at room temperature for 2.5 hours. The ion exchanger was then removed by filtration and the filtrate evaporated to dryness at reduced pressure without heating. The residue was the title compound in the form of a non-crystalline material, obtained in 60% yield. $^1$H NMR (CDCl$_3$): δ4.5–5.0 (2CH$_2$), 5.38 (NCH$_2$), 7.43 (Ph), 8.00 and 8.60 (H-4, H-6, J 4 Hz).

EXAMPLE 21

1-(4-Methyloxycarbonylbenzyloxy)methyl-5-chloropyrimidin-2-one was prepared as described in Example 3 from chloromethyl 4-methyloxycarbonylbenzyl ether (see Preparation 13) (8.8 mmol) and 5-chloropyrimidin-2-one (8.8 mmol) in 62% yield, m.p. 172° C. $^1$H NMR (CDCl$_3$): δ3.92 (OMe), 4.77 (CH$_2$Ph), 5.38 (CH$_2$O), 7.2–8.2 (Ph), 7.78 asnd 8.50 (H-4, H-6, J 4 Hz).

EXAMPLE 22

2,6-Lutidinium 4-[(5-chloro-2-oxopyrimidin-1-yl)methyloxymethyl]-benzyl-2-hydroxyphenyl phosphate A solution of o-phenylene phosphorochloridate (0.33 mmols) in dioxan (2 mls) was added to a pure solution of 1-[(4-hydroxymethyl)benzyloxymethyl]-5-chloropyrimidin-2-one (see Example 20) (0.33 mmols) and 2,6-lutidine (0.33 mmols) in dioxan (6 mls). After 20 minutes 2,6-lutidinium chloride was filtered off and washed with dioxan. The combined filtrate and washings were treated with 2,6-lutidine (0.33 mmols) and water (1.5 mmols). After 10 minutes the solvent was evaporated off under reduced pressure. The residue was washed with ether and insoluble product (160 mg., 92%) was isolated as hygroscopic crystals. $^1$H NMR (deuterated acetonitrile/deuterated chloroform): δ2.68 (CH$_3$— in lutidine), 4.58 (OCH$_2$), 5.08 (CH$_2$—O—PJ 8 HZ), 5.35 (CH$_2$—N), 6.8 to 7.0 (H-3, H-5 of lutidine), 7.1 to 7.6 (phenyl) 7.8 (H-4: J 3 HZ): 7.9 to 8.2 (H-4 in lutidine), 8.50 (H-6: J 3 HZ).

PHARMACEUTICAL COMPOSITION EXAMPLES

EXAMPLE A

| Injection solution | |
|---|---|
| 1. Active ingredient | 50 mg |
| 2. Polysorbate 80 | 2.50 mg |
| 3. Sodium chloride | 45 mg |
| 4. Water for injection | to 5.0 ml |

The sterile active ingredient, precipitated as a very fine powder, is dispersed aseptically in an aqueous vehicle containing the wetting agent (Polysorbate 80) and sufficient sodium chloride to produce an approximately isotonic solution thus providing a suspension which may be used for deep intramuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient together with a sterile ampoule of the remaining ingredients to permit extemporaneous preparation of the suspension immediately before injection.

EXAMPLE B

| Injection solution | |
|---|---|
| 1. Active ingredient | 100 mg |
| 2. Aluminium monostearate | 5 mg |
| 3. Fractionated coconut oil | to 1 ml |

Sterile active ingredient in the form of a very fine powder is dispersed aseptically in a sterile oily vehicle containing a suspending agent whose structure is built up during the heat sterilisation of the vehicle. Such a product may be presented as a pre-prepared suspension for intra-muscular injection. The dose administered may be adjusted by alteration of the dose volume. The product may be presented in multidose vials and sealed with oil resistant rubber plugs to permit withdrawal of the required dose volume.

We claim:

1. A compound of the formula:

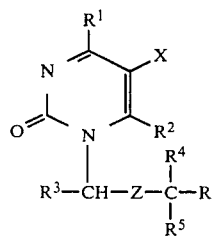

wherein
X represents a halogen atom or a trifluoromethyl group;
$R^1$ and $R^2$, independently represent a hydrogen atom or a lower alkyl group;
$R^3$, $R^4$ and $R^5$, which may be the same or different, each represent a hydrogen atom or a lower alkyl, lower alkenyl, lower alkynyl, lower alkanoyl, lower alkenoyl, $C_{7-16}$ phenylalkyl or naphthylalkyl, or a phenyl or naphthyl group or an unsaturated or aromatic heterocyclic ring having 5 or 6 ring members and having 1–3 hetero-atoms; one or both of $R^4$ and $R^5$ may also represent phenoyl or naphthoyl groups;
Z represents an oxygen atom or a sulfur atom or oxide thereof or a group $NR^6$, wherein $R^6$ is as defined for R hereinafter or represents the group $COR^7$ in which $R^7$ represents a hydrogen atom or a phenyl or naphthyl group, a heterocyclic group having 5 or 6 ring members and having 1–3 hetero-atoms; phenylalkyl, naphthylalkyl, lower alkyl or lower alkoxy group optionally substituted by one or more substituents selected from halogen atoms, hydroxyl, amino, oxo or $C_{1-4}$ alkyl groups; and
R represents a phenyl or naphthyl group or a 5–6 membered unsaturated or aromatic heterocyclic ring which ring contains 1–3 hetero-atoms selected from O, N and S and optionally carries a fused benzene or naphthalene ring and which phenyl or naphthyl group, heterocyclic or heterocyclic ring carrying a fused benzene or naphthalene ring may carry one or more $C_{1-4}$ alkyl or phenyl groups and any one of said groups or rings being optionally substituted by one or more substituents selected from halogen atoms, optionally substituted hydroxyl, optionally substituted amino, nitro, oxo, sulfonic acid and sulfonamido groups and thioether groups and oxides thereof; and where acid or basic groups are present, the salts thereof.

2. A compound as claimed in claim 1 wherein R represents a phenyl or naphthyl group or a 5- or 6-membered heterocyclic ring which group or ring is optionally substituted by one or more substituents selected from halogen atoms and $C_{1-6}$ alkyl, $C_{1-6}$ alkoxy, $C_{1-6}$ haloalkyl, $C_{2-7}$ alkoxycarbonyl, $C_{1-6}$ hydroxyalkyl and $C_{1-6}$ alkylthio groups.

3. A compound as claimed in claim 2 wherein R represents a phenyl, naphthyl, furyl, thienyl, pyrimidinyl or thiadiazolyl group optionally substituted by one or more substituents selected from chlorine atoms and methyl, methoxy, trifluoromethyl, hydroxymethyl, methoxycarbonyl and methylthio groups.

4. A compound as claimed in claim 1 wherein Z represents an oxygen or sulphur atom or the group N—

COR$^7$ in which R$^7$ represents a hydrogen atom or a C$_{1-6}$ alkoxy group.

5. A compound as claimed in claim 1 wherein R$^3$ represents a hydrogen atom.

6. A compound as claimed in claim 1 wherein R$^4$ and R$^5$, which may be the same or different, each represents a hydrogen atom or a C$_{1-6}$ alkyl group.

7. A compound as claimed in claim 1 wherein R$^4$ and R$^5$ each represent a hydrogen atom.

8. A compound as claimed in claim 1 wherein R$^1$ and R$^2$ each represent a hydrogen atom.

9. A compound as claimed in claim 1 wherein X represents a halogen atom.

10. A compound as claimed in claim 1 which is: or 1-(4-Chlorobenzyloxy)methyl-5-chloropyrimidin-2-one and 1-(4-Methoxybenzyloxy)methyl-5-chloropyrimidin-2-one.

11. Pharmaceutical compositions comprising as active ingredient at least one compound of formula I as defined in claim 1 or, where an acidic or basic group is present, a physiologically compatible salt thereof in association with a pharmaceutical carrier or excipient.

12. A method of prophylaxis of abnormal cell proliferation in a host which comprises administering to said host an effective amount of a compound of formula I as defined in claim 1 or, where an acidic or basic group is present, a physiologically compatible salt thereof.

* * * * *